(12) United States Patent
Swanson

(10) Patent No.: US 6,273,906 B1
(45) Date of Patent: Aug. 14, 2001

(54) FOOT CARE DEVICE

(76) Inventor: Jean D. Swanson, 4850 Osprey D.S., #606, St. Petersburg, FL (US) 33711

( * ) Notice: Subject to any disclaimer, the term of this patent is extended or adjusted under 35 U.S.C. 154(b) by 0 days.

(21) Appl. No.: 09/497,300

(22) Filed: Feb. 2, 2000

(51) Int. Cl.[7] .................................................. A61F 7/00
(52) U.S. Cl. ............................ 607/91; 607/88; 607/94
(58) Field of Search ............................. 607/88, 90, 91, 607/93, 94, 95

(56) References Cited

U.S. PATENT DOCUMENTS

| | | | |
|---|---|---|---|
| 3,101,716 | 8/1963 | Cornell, Jr. | 128/375 |
| 4,469,102 | * 9/1984 | Fish | 607/91 |
| 4,582,062 | 4/1986 | Albini | 128/396 |
| 4,623,796 | 11/1986 | Kratz | 250/504 |
| 4,674,507 | 6/1987 | Basso | 128/396 |
| 5,447,528 | 9/1995 | Gerardo | 607/88 |
| 5,466,248 | 11/1995 | Whitson-Newman | 607/88 |
| 5,733,314 | * 3/1998 | Perrino | 607/91 |

* cited by examiner

Primary Examiner—Linda C. M. Dvorak
Assistant Examiner—R. Kearney
(74) Attorney, Agent, or Firm—Joseph N. Breaux

(57) ABSTRACT

A device for tanning the feet of athletes who develop tanned legs while wearing shorts to participate in outdoor activities. The tanning device also includes a fungicidal mechanism for killing foot funguses as well as a foot massaging mechanism for providing soothing vibrations to the feet while the user is receiving a tanning treatment.

1 Claim, 2 Drawing Sheets

FOOT CARE DEVICE

TECHNICAL FIELD

The present invention relates to foot care devices and more particularly to a foot care device that includes a foot receiving housing with two pivoting top panels and an internal foot receiving cavity, an electric motor driven foot vibrator positioned within the internal foot receiving cavity, a tanning lamp assembly positioned within the foot receiving cavity, an anti-fungal lamp assembly positioned within the foot receiving cavity, a timer switch positioned on an exterior surface of the foot receiving housing, and an on/off switch positioned on the exterior surface of the foot receiving housing; the tanning lamp assembly including multiple tanning lamps emitting light in the skin tanning range; the anti-fungal lamp assembly including multiple anti-fungal lamps emitting light in the anti-fungal range; the tanning lamp assembly, and the anti-fungal lamp assembly being wired in parallel with each other and in series with the timer switch; the electric motor driven foot vibrator being wired in series with the on/off switch; each of the two pivoting top panels having two resilient, cushion-lined, half-circular leg passages formed into a top panel side edge thereof; the resilient, cushion-lined, half-circular leg passages being positioned such that when both pivoting top panels are pivoted done into a closed position, each resilient, cushion-lined, half-circular leg passage of one pivoting top panel abuts a resilient, cushion-lined, half-circular leg of the other pivoting top panel such that two full circular leg passages are formed.

BACKGROUND ART

Many individuals who engage in outdoor sports while wearing shorts develop tanned legs. However, because the outdoor sports often require the participant to wear shoes, the feet of the athlete often remain an unattractive pale white. It would be a benefit to these individuals to have a device for tanning the feet. Because athletes often develop foot funguses, it would be a further benefit to these individuals to have a foot tanning device that also included an fungicidal mechanism for killing foot funguses. Because these individuals often have sore and tired feet, it would be a still further benefit to have a foot tanning device that also included a foot massaging mechanism for providing soothing vibrations to the feet.

GENERAL SUMMARY DISCUSSION OF INVENTION

It is thus an object of the invention to provide a foot care device that includes a foot receiving housing with two pivoting top panels and an internal foot receiving cavity, an electric motor driven foot vibrator positioned within the internal foot receiving cavity, a tanning lamp assembly positioned within the foot receiving cavity, an anti-fungal lamp assembly positioned within the foot receiving cavity, a timer switch positioned on an exterior surface of the foot receiving housing, and an on/off switch positioned on the exterior surface of the foot receiving housing; the tanning lamp assembly including multiple tanning lamps emitting light in the skin tanning range; the anti-fungal lamp assembly including multiple anti-fungal lamps emitting light in the anti-fungal range; the tanning lamp assembly, and the anti-fungal lamp assembly being wired in parallel with each other and in series with the timer switch; the electric motor driven foot vibrator being wired in series with the on/off switch; each of the two pivoting top panels having two resilient, cushion-lined, half-circular leg passages formed into a top panel side edge thereof; the resilient, cushion-lined, half-circular leg passages being positioned such that when both pivoting top panels are pivoted done into a closed position, each resilient, cushion-lined, half-circular leg passage of one pivoting top panel abuts a resilient, cushion-lined, half-circular leg of the other pivoting top panel such that two full circular leg passages are formed.

Accordingly, a foot care device is provided. The foot care device includes a foot receiving housing with two pivoting top panels and an internal foot receiving cavity, an electric motor driven foot vibrator positioned within the internal foot receiving cavity, a tanning lamp assembly positioned within the foot receiving cavity, an anti-fungal lamp assembly positioned within the foot receiving cavity, a timer switch positioned on an exterior surface of the foot receiving housing, and an on/off switch positioned on the exterior surface of the foot receiving housing; the tanning lamp assembly including multiple tanning lamps emitting light in the skin tanning range; the anti-fungal lamp assembly including multiple anti-fungal lamps emitting light in the anti-fungal range; the tanning lamp assembly, and the anti-fungal lamp assembly being wired in parallel with each other and in series with the timer switch; the electric motor driven foot vibrator being wired in series with the on/off switch; each of the two pivoting top panels having two resilient, cushion-lined, half-circular leg passages formed into a top panel side edge thereof; the resilient, cushion-lined, half-circular leg passages being positioned such that when both pivoting top panels are pivoted done into a closed position, each resilient, cushion-lined, half-circular leg passage of one pivoting top panel abuts a resilient, cushion-lined, half-circular leg of the other pivoting top panel such that two full circular leg passages are formed.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
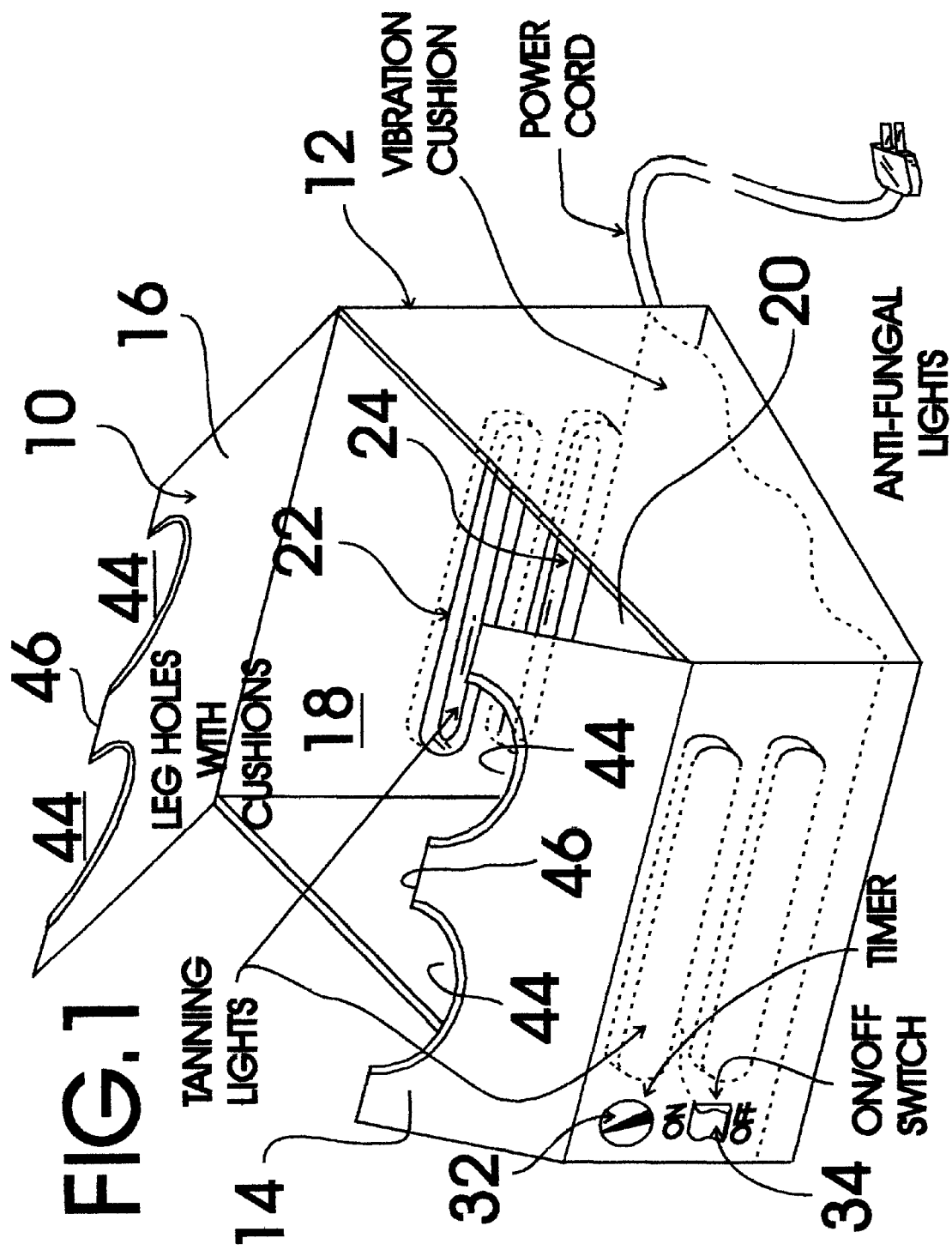
FIG. 1 is a perspective view of an exemplary embodiment of the foot care device of the present invention showing the foot receiving housing with two pivoting top panels and an internal foot receiving cavity, an electric motor driven foot vibrator positioned within the internal foot receiving cavity, a tanning lamp assembly positioned within the foot receiving cavity, an anti-fungal lamp assembly positioned within the foot receiving cavity, a timer switch positioned on an exterior surface of the foot receiving housing, and an on/off switch positioned on the exterior surface of the foot receiving housing; the tanning lamp assembly including multiple tanning lamps emitting light in the skin tanning range; the anti-fungal lamp assembly including multiple anti-fungal lamps emitting light in the anti-fungal range; the tanning lamp assembly, and the anti-fungal lamp assembly being wired in parallel with each other and in series with the timer switch; the electric motor driven foot vibrator being wired in series with the on/off switch; each of the two pivoting top panels having two resilient, cushionlined, half-circular leg passages formed into a top panel side edge thereof; the resilient, cushion-lined, half-circular leg passages being positioned such that when both pivoting top panels are pivoted done into a closed position, each resilient, cushion-lined, half-circular leg passage of one pivoting top panel abuts a resilient, cushion-lined, half-circular leg of the other pivoting top panel such that two circular leg passages are formed.
Figure 2:
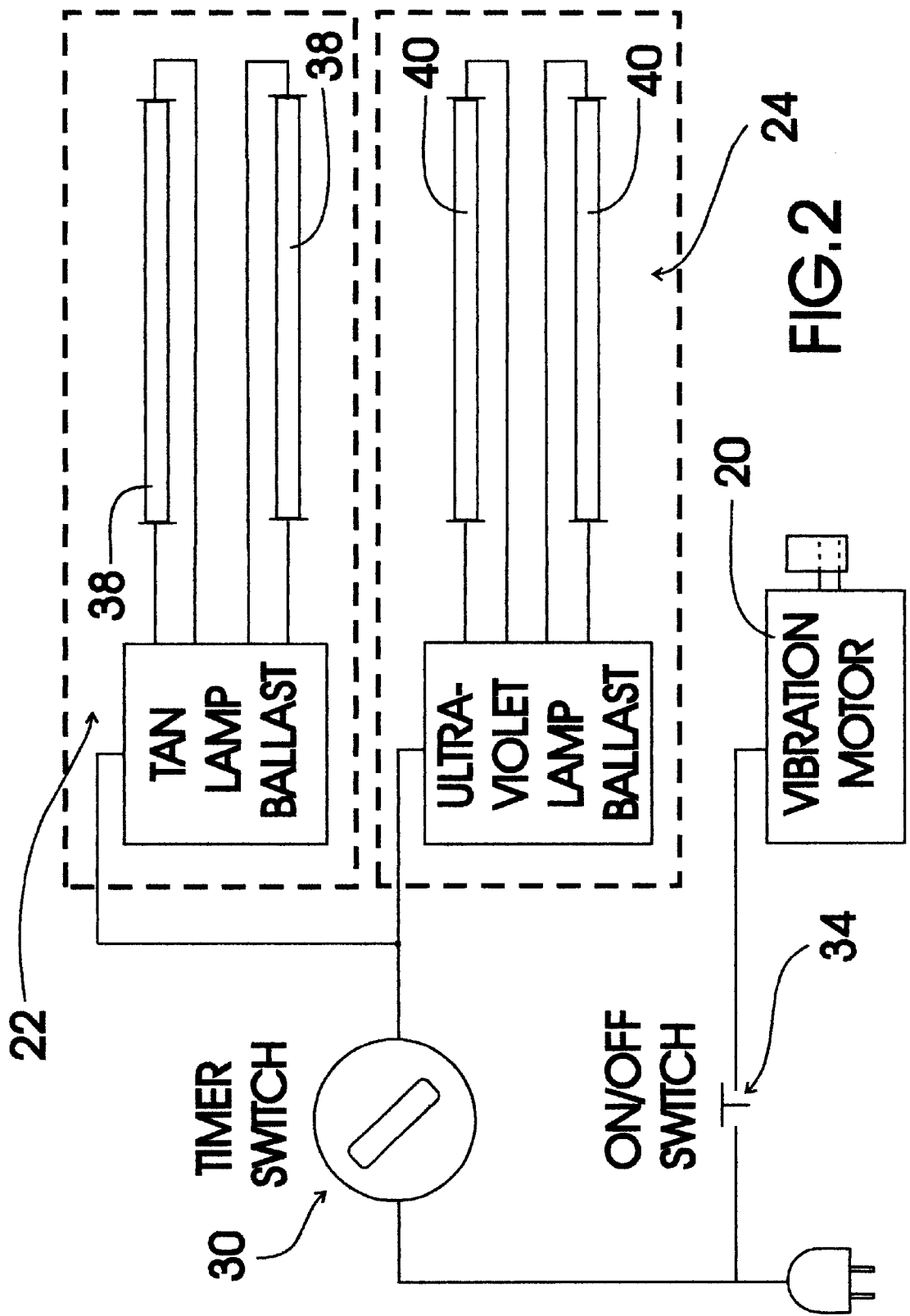
FIG. 2 is a schematic diagram showing the electrical connections between the tanning lamp assembly, the anti-fungal lamp assembly, the electric motor driven foot vibrator, the on/off switch and the timer switch.

FIGS. 1 and 2 show various aspects of an exemplary embodiment of the foot tanning device of the present invention generally designated 10. Foot tanning device 10 includes a foot receiving housing, generally designated 12, with two pivoting top panels 14,16 and an internal foot receiving cavity 18; an electric motor driven foot vibrator 20 positioned within internal foot receiving cavity 18; a tanning lamp assembly, generally designated 22, positioned within foot receiving cavity 18; an anti-fungal lamp assembly, generally designated 24, positioned within foot receiving cavity 18; a timer switch, generally designated 30, positioned on an exterior surface 32 of foot receiving housing 12; and an on/off switch, generally designated 34, positioned on exterior surface 32 of foot receiving housing 12.

Tanning lamp assembly 22 includes two, fluorescent tanning lamps 38 that emit light in the skin tanning range. Anti-fungal lamp assembly 24 includes two fluorescent anti-fungal lamps 40 that emit light in the anti-fungal range. Tanning lamp assembly 22 and anti-fungal lamp assembly 24 are wired in parallel with each other and in series with timer switch 30. Electric motor driven foot vibrator 20 is wired in series with on/off switch 34.

Each of the two pivoting top panels 14,16 has two resilient, cushion-lined, half-circular leg passages 44 formed into a top panel side edge 46 thereof. The resilient, cushion-lined, half-circular leg passages 44 are positioned such that when both pivoting top panels 14,16 are pivoted done into a closed position, each resilient, cushion-lined, half-circular leg passage 44 of one pivoting top panel 14,16 abuts a resilient, cushion-lined, half-circular leg passage 44 of the other pivoting top panel 14,16 such that two full circular leg passages are formed.

It can be seen from the preceding description that a foot care device has been provided.

It is noted that the embodiment of the foot care device described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A foot care device comprising:

a foot receiving housing with two pivoting top panels and an internal foot receiving cavity;

an electric motor driven foot vibrator positioned within said internal foot receiving cavity;

a tanning lamp assembly positioned within said foot receiving cavity;

an anti-fungal lamp assembly positioned within said foot receiving cavity;

a timer switch positioned on an exterior surface of said foot receiving housing; and an on/off switch positioned on said exterior surface of said foot receiving housing;

said tanning lamp assembly including multiple tanning lamps emitting light in said skin tanning range;

said anti-fungal lamp assembly including multiple anti-fungal lamps emitting light in said anti-fungal range;

said tanning lamp assembly and said anti-fungal lamp assembly being wired in parallel with each other and in series with said timer switch;

said electric motor driven foot vibrator being wired in series with said on/off switch;

each of said two pivoting top panels having two resilient, cushion-lined, half-circular leg passages formed into a top panel side edge thereof;

said resilient, cushion-lined, half-circular leg passages being positioned such that when both pivoting top panels are pivoted done into a closed position, each resilient, cushion-lined, half-circular leg passage of one pivoting top panel abuts a resilient, cushion-lined, half-circular leg of said other pivoting top panel such that two full circular leg passages are formed.

* * * * *